United States Patent [19]

Franz

[11] Patent Number: Plant 6,217

[45] Date of Patent: Jul. 12, 1988

[54] YEW NAMED GWEN

[76] Inventor: Lloyd W. Franz, Rte. 3, Napoleon, Ohio 43545

[21] Appl. No.: 785,240

[22] Filed: Oct. 7, 1985

[51] Int. Cl.[4] ..... A01H 5/00

[52] U.S. Cl. ..... Plt./50

[58] Field of Search ..... Plt. 50

[56] References Cited

PUBLICATIONS

Harrison, C. R., "*Taxus×media*", *Ornamental Conifers* (p. 159), pub. 1975 by A. H. & A. W. Reed Ltd., Wellington, N.Z.

Duden, P. D. et al, "*Taxus media*", *Manual of Cultivated Confers*, pub. 1965 by The Hague/Martinus Nijhoff (pp. 411 and 412).

Kumlien, L. L., "Hicks Yew (*Taxus media hicksi*), *The Friendly Evergreens*, pub: D. Hill Nursery Co., Dunder, Ill., 1946, (p. 210).

Wyman, D., *Shrubs and Vines for American Gardens*, Macmillan Publishing Co. Inc., N.Y., 1973, p. 462.

*Primary Examiner*—James R. Feyrer

*Attorney, Agent, or Firm*—Charles W. Rummler

[57] ABSTRACT

A new variety from dwarf Taxus or Hicksi yew particularly distinguished by its very hardy and compact naturally global growth habit and its much richer color than other plants of the hicksi family. Also, this new plant readily withstands the harshest weather conditions and has no signs of winter or spring burn which affects other plants grown in the same open areas in which my new plant is cultivated.

1 Drawing Sheet

BACKGROUND OF THE NEW PLANT

My new variety of yew was discovered as a whole plant sport or mutation appearing among a field of these dwarf Taxus plants being grown in my nursery for many years at Napoleon, Ohio, this new plant having been discovered by me in 1968. Propagation of this new plant has been carried on by me by means of cuttings at Napoleon, Ohio, and successive generations grown over the past fifteen years have shown that the novel characteristics of the discovery plant are fully retained and appear to be firmly fixed.

I have propagated my new yew year after year by means of cuttings and specimens at least ten years old have been grown for experimental purposes in several parts of this country for testing to determine its hardiness under various environmental growing conditions and as the result of such successful testing and more than fifteen years of continuous propagation, I have now determined that this new variety is ready for commercial sale and release under license to interested growers of dwarf Taxus plants for ornamental use.

DESCRIPTION OF THE DRAWING

My new dwarf Taxus, or yew, is illustrated by the accompanying drawing on which the left hand view shows the discovery plant at the age of about twenty-five years and its naturally globular growth habit; and the right hand view shows a cutting of the new plant at the age of about eight years prepared for transplanting and shipment.

DESCRIPTION OF THE NEW PLANT

The following is a description of my new yew based upon observations of the discovery plant and its propagated clones, the observations having been made at several times since the winter of 1984–1985 at Napoleon, Ohio, and the color designations being according to The R.H.S. Colour Chart of The Royal Horticultural Society of London, England.

Origin: Sport.

Parentage: Unknown. This whole plant originated in an open field of nursery grown Hicksi yew plants being developed for eventual commercialization.

Classification:

*Botanic.*—*Taxus media* Yew.

*Commercial.*—Hicksi Yew family.

Form: Bush of global shape, after about six to eight years of growth.

Size of 25 year old plant:

*Height.*—About 22 to 25 inches.

*Shape.*—Globular.

*Diameter.*—About 22 inches.

*Trunk size.*—About 2 inches in diameter.

*Strength.*—Very hardy.

*Growth rate.*—About ½ inch per year.

Branches:

*Size.*—About 8 to 10 inches long.

*Attachment angle.*—Upright.

*Spacing.*—Very compact and much closer than branches of the Hicksi family.

Lenticels:

*Quantity.*—About 20 to 25 on the main stem.

*Size.*—About one-fourth inch diameter.

Needles: Linear, narrow, flat and pointed. About one to one and one-fourth inch long and about 0.035 inches thick.

*Color.*—Upper side — RHS 147A. Under side — RHS 146B.

This new yew plant has a much richer color than the plants of which this is a sport. These new plants are being grown in open areas exposed to the harshest weather conditions and are thus found to be much hardier than those of which it is a sport. It is a very compact grower, very slow dwarf in growth habit, and requires very little care in trimming to keep it in its natural compact global form. This new plant does well in all types of well drained soils and of at least fourteen varieties of Taxus now growing in my nursery operation, this new plant is the hardiest of all and retains its distinction of having a much richer color than the variety of which this plant is a sport.

I claim:

1. A new and distinct variety of yew substantially as herein shown and described and particularly distinguished by its richer color than its companion plants growing in the same environment, and by its very slow, naturally global growth habit.

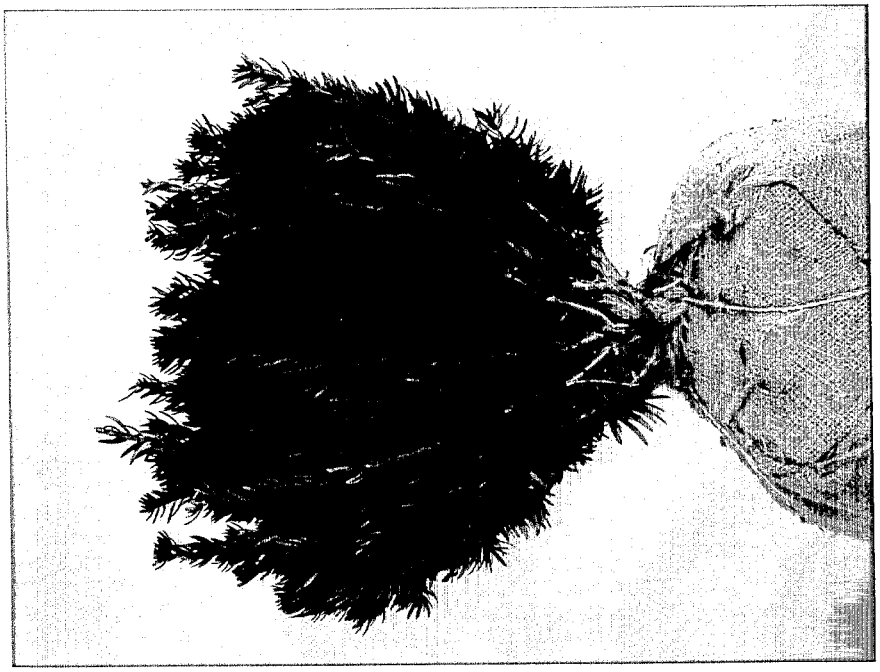
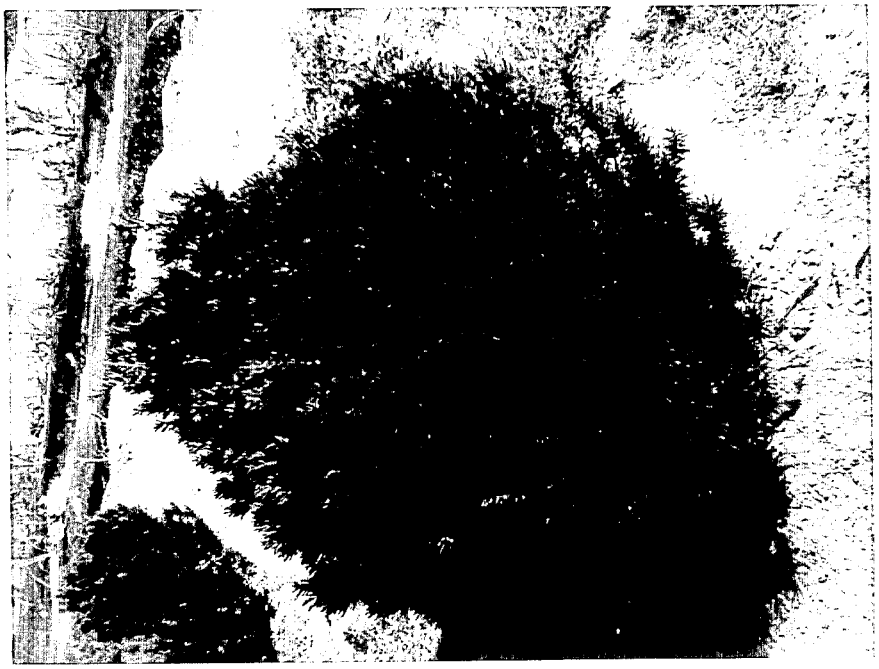

* * * * *